United States Patent
Bryans et al.

(10) Patent No.: US 6,245,801 B1
(45) Date of Patent: Jun. 12, 2001

(54) BRANCHED ALKYL PYRROLIDINE-3-CARBOXYLIC ACIDS

(75) Inventors: Justin Stephen Bryans, Balsham (GB); Ihoezo Victor Ekhato, Ann Arbor, MI (US); David Christopher Horwell, Cambridge (GB); Rong Ling, Ann Arbor, MI (US); Jean-Marie Receveur, Cambridge (GB); David Juergen Wustrow, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/673,277
(22) PCT Filed: Aug. 11, 1999
(86) PCT No.: PCT/US99/18258
  § 371 Date: Oct. 13, 2000
  § 102(e) Date: Oct. 13, 2000
(87) PCT Pub. No.: WO00/15611
  PCT Pub. Date: Mar. 23, 2000

Related U.S. Application Data
(60) Provisional application No. 60/100,156, filed on Sep. 14, 1998.

(51) Int. Cl.$^7$ ............ A61K 31/40; A61P 25/08; C07D 207/04
(52) U.S. Cl. ............................ 514/423; 548/572
(58) Field of Search ............... 548/572; 514/423

(56) References Cited

U.S. PATENT DOCUMENTS 4,087,544  5/1978  Satzinger et al. .

FOREIGN PATENT DOCUMENTS 96 06095  2/1996  (WO) .
96 15108  5/1996  (WO) .

*Primary Examiner*—Deborah C. Lambkin
*Assistant Examiner*—Andrea M D'Souza
(74) *Attorney, Agent, or Firm*—Elizabeth M. Anderson

(57) ABSTRACT

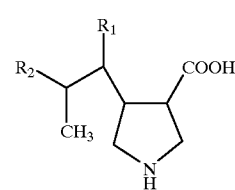

Branched alkyl pyrrolidines of formula (I) are disclosed and are useful as agents in the treatment of epilepsy, faintness attacks, hypokinesia, cranial disorders, neurodegenerative disorders, depression, anxiety, panic, pain, and neuropatnological disorders. Processes for the preparation and intermediates useful in the preparation are also disclosed.

16 Claims, No Drawings

BRANCHED ALKYL PYRROLIDINE-3-CARBOXYLIC ACIDS

This appln. is a 371 of PCT/US99/18258 Aug. 11, 1999 which claims benefit of 60/100,156 Sep. 14, 1998.

BACKGROUND OF THE INVENTION

Compounds of formula

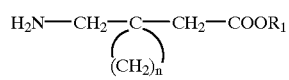

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

SUMMARY OF THE INVENTION

The compounds, prodrugs, and pharmaceutically acceptable salts are useful in a variety of disorders. The disorders include: convulsions such as in epilepsy, faintness attacks, hypokinesia, cranial disorders, neurodegenerative disorders, depression, anxiety, panic, pain, inflammatory disorders such as arthritis, irritable bowel syndrome, and neuropathological disorders.

The compounds are those of formula

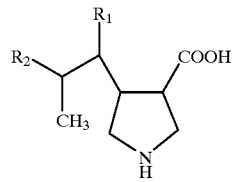

or a pharmaceutically acceptable salt thereof or a prodrug thereof wherein $R_1$ is hydrogen or a straight or branched alkyl of from 1 to 5 carbons;

$R_2$ is a straight or branched alkyl of from 1 to 5 carbons; and $R_1$ and $R_2$ when taken together form a carbocyclic ring of from 3 to 7 atoms.

Preferred compounds are those wherein $R_1$ is H, methyl, or ethyl; and $R_2$ is methyl or ethyl.

The most preferred compounds are those wherein (cis)-4-isobutyl-pyrrolidine-3-carboxylic acid and (trans)-4-isobutyl-pyrrolidine-3-carboxylic acid.

Other preferred compounds are those wherein $R_1$ and $R_2$ are taken to form a carbocyclic ring of from 3 to 7 atoms.

More preferred compounds are those wherein $R_1$ and $R_2$ form a five or six membered ring.

Novel intermediates useful in the preparation of the final compounds are also encompassed by the invention.

Other compounds of the invention are those of Formula IA

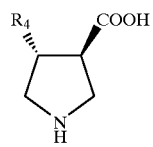

or a pharmaceutically acceptable salt thereof wherein $R_4$ is alkyl of 3 or 4 carbons. Such compounds are selected from:

trans-4-isopropylpyrrolidine-3-carboxylic acid;
trans-4-propyl-pyrrolidine-3-carboxylic acid; and
trans-4-butyl-pyrrolidine-3-carboxylic acid.

DETAILED DESCRIPTION OF THE INVENTION

The compounds of the instant invention and their pharmaceutically acceptable salts and prodrugs are as defined by Formula I above.

The term "alkyl" is a straight or branched group of from 1 to 5 carbon atoms including but not limited to methyl, ethyl, propyl, n-propyl, isopropyl, butyl, 2-butyl, tert-butyl, and pentyl.

Preferred groups are methyl and tert-butyl.

The stereocenters in Formula I can have independently be of either an R or S configuration.

Compounds of Formula I wherein the two substituents have a cis relative orientation about the pyrrolidine ring can be prepared in the following manner outlined in Scheme 1.

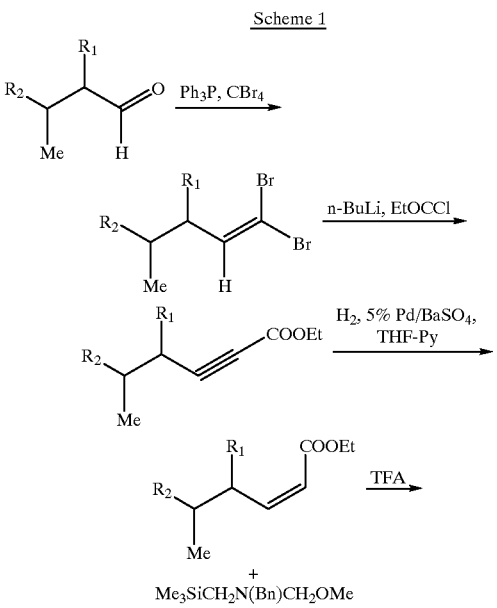

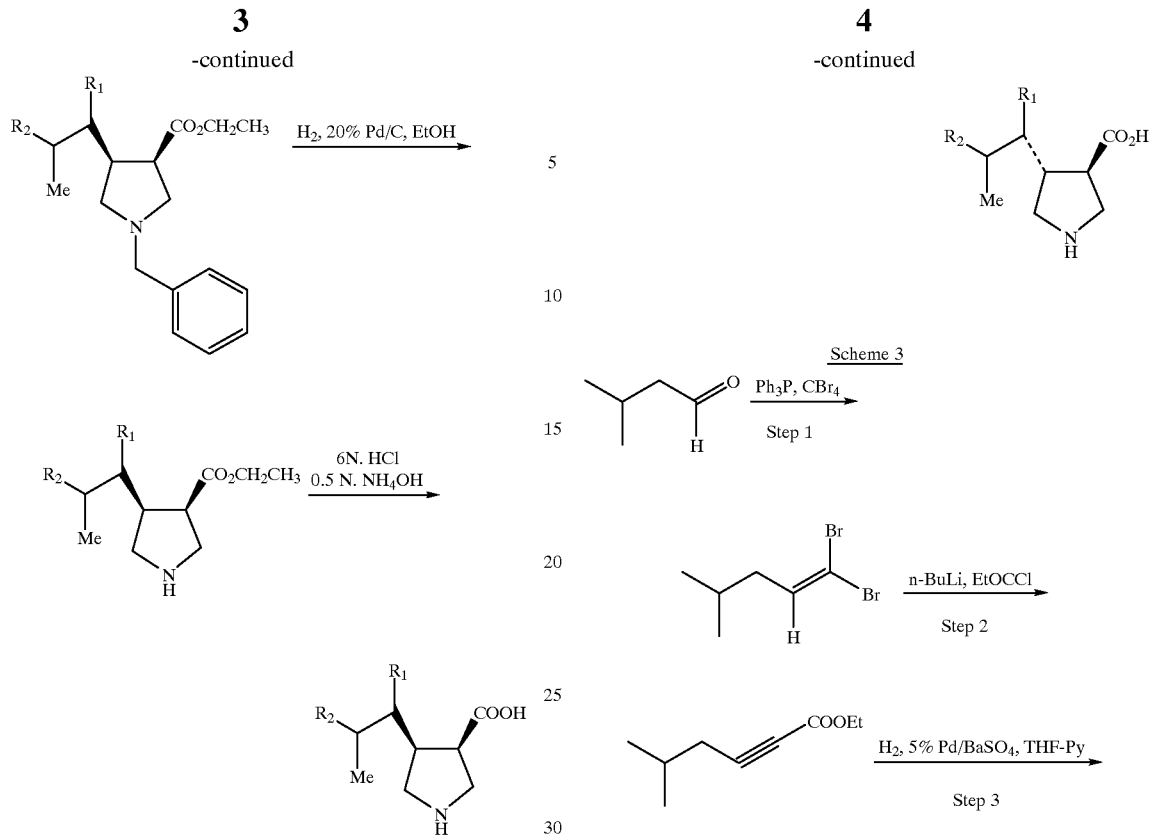
Compounds of Formula I wherein the two substituents have a trans relative orientation about the pyrrolidine ring, can be prepared in the following manner outlined in Scheme 2.
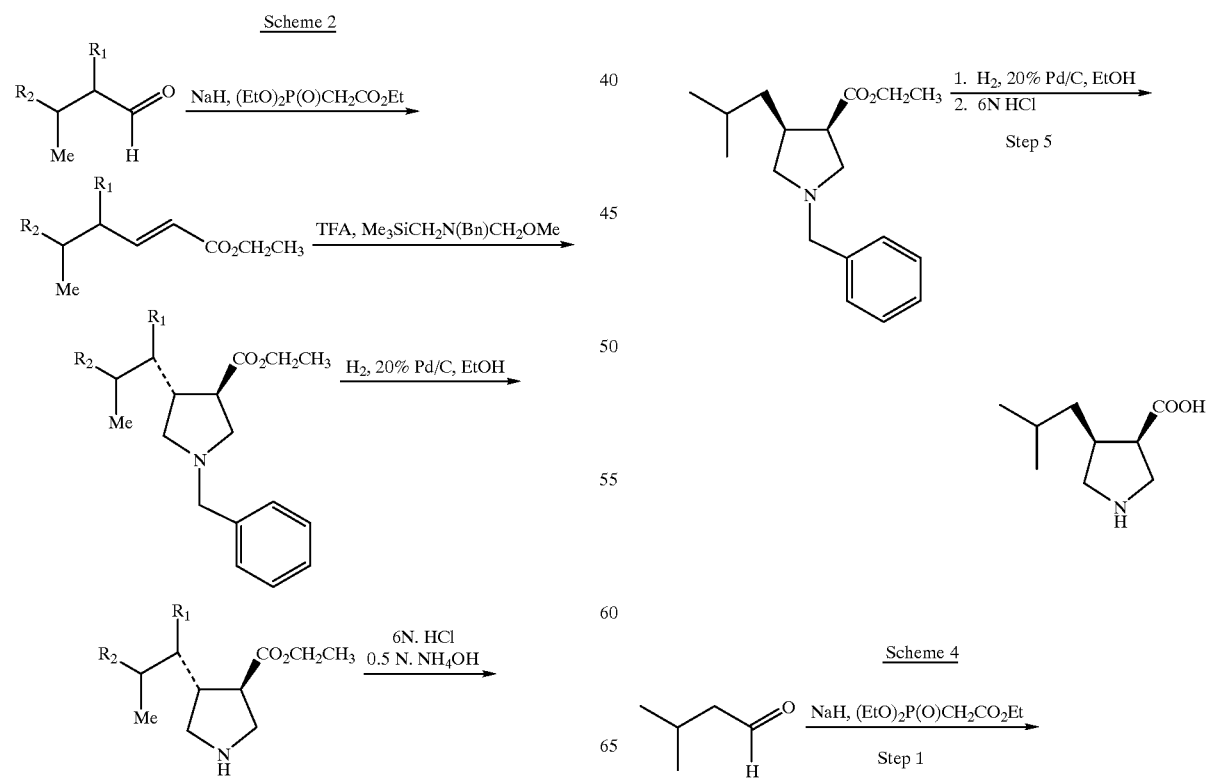

-continued
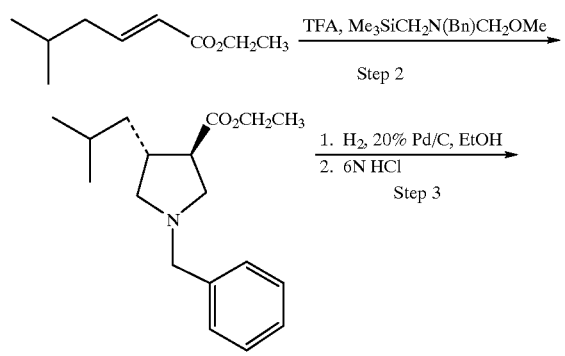
Scheme 6
1. oxalyl chloride, DMF, Toluene, r.t
2. NaH, (S)-4-phenyl-2-oxazolidinone
   THF, 0° C.
   100%
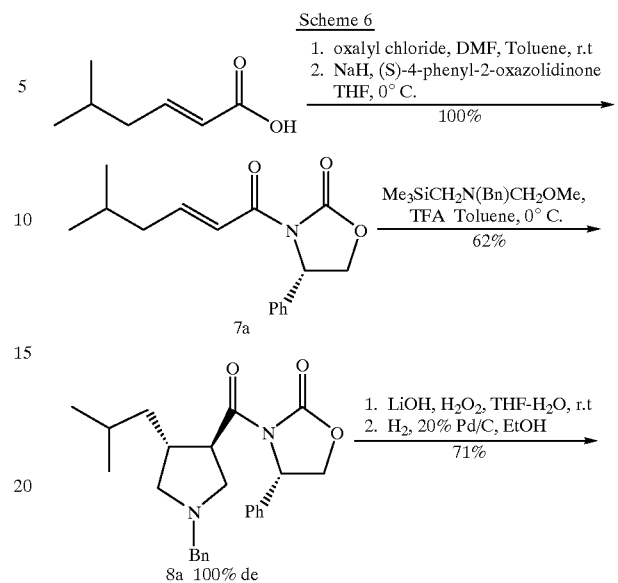
Scheme 5
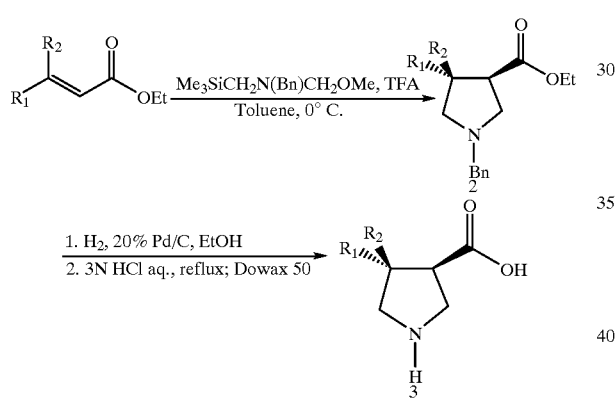
| Compound | R₁ | R₂ | 2 (%) | 3 (%) |
|---|---|---|---|---|
| a | CH₃ | H | 100 | 90 |
| b | CH₃ | CH₃ | 28 | 84 |
| c | C₂H₅ | H | 95 | 78 |
| d | i-Pr | H | 79 | 88 |
| e | n-Pr | H | 72 | 88 |
| f | i-Bu | H | 99 | 86 |
| g | H | i-Bu | 41 | 85 |
| h | n-Bu | H | 82 | 85 |
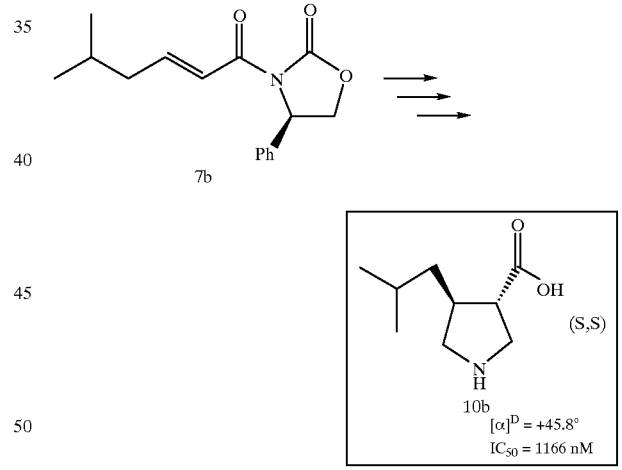
TABLE I
| Structure | [3H]GAP Binding IC₅₀ (μM) | NA Release % Inhibition @ 100 μM | Sys L IC₅₀ (μM) | CITH % MPE 1 h | 2 h | DBA 2 % Protect (time) | Vogel % of CI-1008 |
|---|---|---|---|---|---|---|---|
| 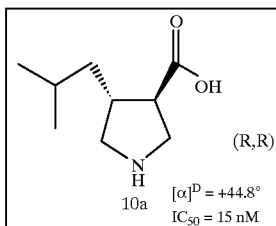 gabapentin | 0.140 | | 25 | 48.9 | 19.9 | 100 | 63.7 |

TABLE I-continued

| Structure | [3H]GAP Binding IC$_{50}$ ($\mu$M) | NA Release % Inhibition @ 100 $\mu$M | Sys L IC$_{50}$ ($\mu$M) | CITH % MPE 1 h | 2 h | DBA 2 % Protect (time) | | Vogel % of C1-1008 |
|---|---|---|---|---|---|---|---|---|
| pregabalin | 0.087 | | 193 | 52.5 | 50.1 | 100 | 100 | 100 |
| spirocyclic (R) | 0.120 | | >10,000 | 53 | 4.6 | 20 | 20 | |
| isobutyl pyrrolidine (+/-) | 0.051 | | | 3 | -15 | 0 | 0 | |
| isobutyl pyrrolidine (+/-) | 0.700 | | | 23 | 3.3 | 0 | 0 | |
| isobutyl pyrrolidine (R,R) | 0.015 | 16 | | | | 20 | 40 | 0.63 |
| isobutyl pyrrolidine (S,S) | 1.166 | 8 | | | | | | -0.63 |
| methyl pyrrolidine | 3.101 | | | | | | | |
| methyl pyrrolidine | 1.192 | | | | | | | |
| ethyl pyrrolidine | | | | | | | | |

TABLE I-continued

| | [3H]GAP Binding | NA Release % Inhibition | Sys L | CITH % MPE | | DBA 2 % Protect | Vogel % of |
|---|---|---|---|---|---|---|---|
| Structure | IC$_{50}$ ($\mu$M) | @ 100 $\mu$M | IC$_{50}$ ($\mu$M) | 1 h | 2 h | (time) | C1-1008 |
| 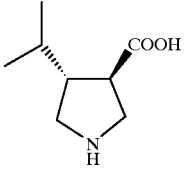 | 0.543 | | | | | | |
| 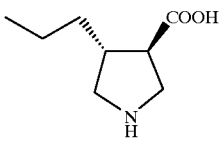 | 0.030 | | | | | | |
| 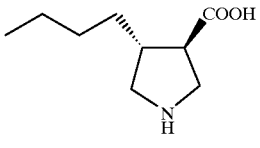 | 0.064 | | | | | | |

Since amino acids are amphoteric, pharmacologically compatible salts when R is hydrogen can be salts of appropriate inorganic or organic acids, for example, hydrochloric, sulphuric, phosphoric, acetic, oxalic, lactic, citric, malic, salicylic, malonic, maleic, succinic, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion.

Prodrugs of compounds I–VIII are included in the scope of the instant invention. Aminoacyl-glycolic and -lactic esters are known as prodrugs of amino acids (Wermuth C. G., *Chemistry and Industry*, 1980:433–435). The carbonyl group of the amino acids can be esterified by known means. Prodrugs and soft drugs are known in the art (Palomino E., *Drugs of the Future*, 1990;15(4):361–368). The last two citations are hereby incorporated by reference.

The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a prodrug form.

A prodrug is a drug which has been chemically modified and may be biologically inactive at its site of action, but which may be degraded or modified by one or more enzymatic or other in vivo processes to the parent bioactive form.

This chemically modified drug, or prodrug, should have a different pharmacokinetic profile to the parent, enabling easier absorption across the mucosal epithelium, better salt formulation and/or solubility, improved systemic stability (for an increase in plasma half-life, for example). These chemical modifications may be 1) ester or amide derivatives which may be cleaved by, for example, esterases or lipases. For ester derivatives, the ester is derived from the carboxylic acid moiety of the drug molecule by known means. For amide derivatives, the amide may be derived from the carboxylic acid moiety or the amine moiety of the drug molecule by known means.
2) peptides which may be recognized by specific or non-specific proteinases. A peptide may be coupled to the drug molecule via amide bond formation with the amine or carboxylic acid moiety of the drug molecule by known means.
3) derivatives that accumulate at a site of action through membrane selection of a prodrug form or modified prodrug form,
4) any combination of 1 to 3.

Current research in animal experiments has shown that the oral absorption of certain drugs may be increased by the preparation of "soft" quaternary salts. The quaternary salt is termed a "soft" quaternary salt since, unlike normal quaternary salts, e.g., R—N$^+$(CH$_3$)$_3$, it can release the active drug on hydrolysis.

"Soft" quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the "soft" quaternary salt has surfactant properties and is capable of forming micelles and unionized ion pairs with bile acids, etc., which are able to penetrate the intestinal epithelium more effectively. The prodrug, after absorption, is rapidly hydrolyzed with release of the active parent drug.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. For example, the compound of Example 1 is a mixture of all four possible stereoisomers. The compound of Example 6 is one of the isomers. The configuration of the cyclohexane ring carbon centers may be R or S in these compounds where a configuration can be defined.

The radioligand binding assay using [$^3$H]gabapentin and the $\alpha_2\delta$ subunit derived from porcine brain tissue was used (Gee N. S., Brown J. P., Dissanayake V. U. K., Offord J., Thurlow R., Woodruff G. N., "The Novel Anti-convulsant Drug, Gabapentin, Binds to the $\alpha_2\delta$ Subunit of a Calcium Channel," *J. Biol. Chem.*, 1996;271:5879–5776).

Compounds can also be assayed for biological activity using a [3H]gabapentin binding assay as described in Suman Chauhan N., et al., *Eur. J. Pharmacol.*, 1993;244:293–301.

TABLE 2

| Compound | Structure | IC$_{50}$ ($\mu$M) at $\alpha_2\delta$ Binding Site |
|---|---|---|
| Example 1 | ![structure] | 0.135 |
| Example 2 | ![structure] | 0.044 |

Table 2 above shows the binding affinity of the compounds of the invention to the $\alpha_2\delta$ subunit.

The compounds of the invention are compared to Neurontin®, a marketed drug effective in the treatment of such disorders as epilepsy. Neurontin® is 1-(aminomethyl)-cyclohexaneacetic acid of structural formula

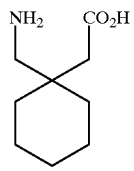

Gabapentin (Neurontin®) is about 0.10 to 0.12 $\mu$M in this assay. The compounds of the instant invention are expected, therefore, to exhibit pharmacologic properties comparable to gabapentin. For example, as agents for convulsions, anxiety, and pain.

The present invention also relates to therapeutic use of the compounds of the mimetic as agents for neurodegenerative disorders.

Such neurodegenerative disorders are, for example, Alzheimer's disease, Huntington's disease, Parkinson's disease, and Amyotrophic Lateral Sclerosis.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia. A patient undergoing carotid endarterectomy specifically or other cerebrovascular or vascular surgical procedures in general, or diagnostic vascular procedures including cerebral angiography and the like.

Other incidents are head trauma, spinal cord trauma, or injury from general anoxia, hypoxia, hypoglycemia, hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

Pain refers to acute as well as chronic pain.

Acute pain is usually short-lived and is associated with hyperactivity of the sympathetic nervous system. Examples are postoperative pain and allodynia.

Chronic pain is usually defined as pain persisting from 3 to 6 months and includes somatogenic pains and psychogenic pains. Other pain is nociceptive.

Still other pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, atypical facial pain, and chronic headache.

Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, bum, and other forms of neuralgia, neuropathic and idiopathic pain syndrome.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems likely that GABA-mimetics might decrease or inhibit cerebral function and might therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

MATERIAL AND METHODS

Carrageenin-Induced Hyperalgesia

Nociceptive pressure thresholds were measured in the rat paw pressure test using an analgesymeter (Randall-Selitto method: Randall L. O. and Selitto J. J., "A method for measurement of analgesic activity on inflamed tissue," *Arch. Int. Pharmacodyn.*, 1957;4:409–419). Male Sprague-Dawley rats (70–90 g) were trained on this apparatus before the test day. Pressure was gradually applied to the hind paw of each rat and nociceptive thresholds were determined as the pressure (g) required to elicit paw withdrawal. A cutoff point of 250 g was used to prevent any tissue damage to the paw. On the test day, two to three baseline measurements were taken before animals were administered 100 $\mu$L of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg, s.c.), morphine (3 mg/kg, s.c.) or saline at 3.5 hours after carageenin and nociceptive thresholds were examined at 4, 4.5, and 5 hours postcarrageenin.

(R)-2-Aza-spiro[4.5]decane-4-carboxylic acid hydrochloride was tested in the above carrageenan-induced hyperalgesia model. The compound was dosed orally at 30 mg/kg, and 1 hour postdose gave a percent of maximum possible effect (MPE) of 53%. At 2 hours postdose, it gave only 4.6% of MPE.

Compounds can be tested for antihyperalgesic activity using the method described in Bennett G. J., et al., *Pain*, 1988;33:87–107.

Mouse Light/Dark Box

The apparatus is an open-topped box, 45 cm long, 27 cm wide, and 27 cm high, divided into a small (2/5) and a large (3/5) area by a partition that extended 20 cm above the walls (Costall B., et al., "Exploration of mice in a black and white box: validation as a model of anxiety," *Pharmacol. Biochem. Behav.*, 1989;32:777–785).

There is a 7.5×7.5 cm opening in the center of the partition at floor level. The small compartment is painted black and the large compartment white. The white compartment is illuminated by a 60-W tungsten bulb. The laboratory is illuminated by red light. Each mouse is tested by placing it in the center of the white area and allowing it to explore the novel environment for 5 minutes. The time spent in the illuminated side is measured (Kilfoil T., et al., "Effects of anxiolytic and anxiogenic drugs on exploratory activity in a simple model of anxiety in mice," *Neuropharmacol*, 1989;28:901–905).

Rat Elevated X-Maze

A standard elevated X-maze (Handley S.L., et al., "Effects of alpha-adrenoceptor agonists and antagonists in a maze-exploration model of 'fear'-motivated behavior," *Naunyn-Schiedeberg's Arch. Pharmacol.*, 1984;327:1–5), was automated as previously described (Field, et al., "Automation of the rat elevated X-maze test of anxiety," *Br. J. Pharmacol.*, 1991;102(Suppl.):304P). The animals are placed on the center of the X-maze facing one of the open arms. For determining anxiolytic effects the entries and time spent on the end half sections of the open arms is measured during the 5-minute test period (Costall, et al., "Use of the elevated plus maze to assess anxiolytic potential in the rat," *Br. J. Pharmacol.*, 1989;96(Suppl.):312p).

Marmoset Human Threat Test

The total number of body postures exhibited by the animal towards the threat stimulus (a human standing approximately 0.5 m away from the marmoset cage and staring into the eyes of the marmoset) is recorded during the 2-minute test period. The body postures scored are slit stares, tail postures, scent marking of the cage/perches, piloerection, retreats, and arching of the back. Each animal is exposed to the threat stimulus twice on the test day before and after drug treatment. The difference between the two scores is analyzed using one-way analysis of variance followed by Dunnett's t-test. All drug treatments are carried out SC at least 2 hours after the first (control) threat. The pretreatment time for each compound is 40 minutes.

Rat Conflict Test

Rats are trained to press levers for food reward in operant chambers. The schedule consists of alternations of four 4-minute unpunished periods on variable interval of 30 seconds signaled by chamber lights on and three 3-minute punished periods on fixed ratio 5 (by footshock concomitant to food delivery) signaled by chamber lights off. The degree of footshock is adjusted for each rat to obtain approximately 80% to 90% suppression of responding in comparison with unpunished responding. Rats receive saline vehicle on training days.

DBA2 Mouse Model of Anticonvulsant Efficacy

All procedures were carried out in compliance with the NIH Guide for the Care and Use of Laboratory Animals under a protocol approved by the Parke-Davis Animal Use Committee. Male DBA/2 mice, 3 to 4 weeks old were obtained from Jackson Laboratories Bar Harbour, Me. Immediately before anticonvulsant testing, mice were placed upon a wire mesh, 4 inches square, suspended from a steel rod. The square was slowly inverted through 180° and mice observed for 30 seconds. Any mouse falling from the wire mesh was scored as ataxic (Coughenour L. L., McLean J. R., Parker R. B., "A new device for the rapid measurement of impaired motor function in mice," *Pharm. Biochem. Behav.*, 1977;6(3):351–3). Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for one minute. DBA/2 mice in the vehicle-treated group responded to the sound stimulus (applied until tonic extension occurred, or for a maximum of 60 sec) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15 to 20 seconds. The incidence of all the seizure phases in the drug-treated and vehicle-treated mice was recorded, and the occurrence of tonic seizures were used for calculating anticonvulsant $ED_{50}$ values by probit analysis (Litchfield J. T., Wilcoxon F. "A simplified method for evaluating dose-effect experiments," *J. Pharmacol.*, 1949;96:99–113). Mice were used only once for testing at each dose point. Groups of DBA/2 mice (n=5–10 per dose) were tested for sound-induced seizure responses 2 hours (previously determined time of peak effect) after given drug orally. All drugs in the present study were dissolved in distilled water and given by oral gavage in a volume of 10 mL/kg of body weight. Compounds that are insoluble will be suspended in 1% carboxymethocellulose. Doses are expressed as weight of the active drug moiety.

The compounds of the instant invention are also expected to be useful in the treatment of pain and phobic disorders (*Am. J. Pain Manag.*, 1995;5:7–9).

The compounds of the instant invention are also expected to be useful in treating the symptoms of manic, acute or chronic, single upside, or recurring depression. They are also expected to be useful in treating and/or preventing bipolar disorder (U.S. Pat. No. 5,510,381).

Models of Irritable Bowel Syndrome
TNBS-Induced Chronic Visceral Allodynia In Rats Injections of trinitrobenzene sulfonic (TNBS) into the colon have been found to induce chronic colitis. In human, digestive disorders are often associated with visceral pain. In these pathologies, the visceral pain threshold is decreased indicating a visceral hypersensitivity. Consequently, this study was designed to evaluate the effect of injection of TNBS into the colon on visceral pain threshold in a experimental model of colonic distension.

MATERIALS AND METHODS

Animals and Surgery

Male Sprague-Dawley rats (Janvier, Le Genest-St-Ilse, France) weighing 340–400 g are used. The animals are housed 3 per cage in a regulated environment (20±1° C., 50±5% humidity, with light 8:00 am to 8:00 pm). Under anesthesia (ketamine 80 mg/kg i.p; acepromazin 12 mg/kg ip), the injection of TNBS (50 mg/kg) or saline (1.5 mL/kg) is performed into the proximal colon (1 cm from the cecum). After the surgery, animals are individually housed in polypropylene cages and kept in a regulated environment (20±1° C., 50±5% humidity, with light 8:00 am to 8:00 pm) during 7 days.

Experimental Procedure

At Day 7 after TNBS administration, a balloon (5–6 cm length) is inserted by anus and kept in position (tip of balloon 5 cm from the anus) by taping the catheter to the base of the tail. The balloon is progressively inflated by step of 5 mm Hg, from 0 to 75 mm Hg, each step of inflation lasting 30 seconds. Each cycle of colonic distension is controlled by a standard barostat (ABS, St-Dié, France). The threshold corresponds to the pressure which produced the first abdominal contraction and the cycle of distension is then discontinued. The colonic threshold (pressure expressed in mm Hg) is determined after performance of four cycles of distension on the same animal.

Determination of the Activity of the Compound

Data is analyzed by comparing test compound-treated group with TNBS-treated group and control group. Mean and sem are calculated for each group. The antiallodynic activity of the compound is calculated as follows:

Activity (%)=(group C−group T)/(group A−group T)
  Group C: mean of the colonic threshold in the control group
  Group T: mean of the colonic threshold in the TNBS-treated group
  Group A: mean of the colonic threshold in the test compound-treated group Statistical Analysis Statistical significance between each group was determined by using a one-way ANOVA followed by Student's unpaired t-test. Differences were considered statistically significant at $p<0.05$.

Compounds

TNBS is dissolved in EtOH 30% and injected under a volume of 0.5 mL/rat. TNBS is purchased from Fluka.

Oral administration of the test compound or its vehicle is performed 1 hour before the colonic distension cycle.

Sub-cutaneous administration of the test compound or its vehicle is performed 30 minutes before the colonic distension cycle.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparations" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such formn the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following examples are illustrative of the synthetic procedures for making the intermediates and final products of the instant invention. They are not intended to limit the scope of the invention.

EXAMPLE 1

(cis)-4-Isobutyl-pyrrolidine-3-carboxylic acid (see Scheme 3)

Step 1: Synthesis of 1,1-Dibromo-4-methyl-pent-1-ene

To a stirred solution of carbon tetrabromide (30 g, 90.63 mmol) in dichloromethane (400 mL) at −10° C. was added triphenylphosphine (60 g, 229 mmol) in portions. Internal temperature was kept below 5° C. during the addition, and it was stirred for additional 30 minutes at this temperature after the addition was completed. Isovaleraldehyde 1 (9.4 mL, 87.6 mmol) in methylene chloride (50 mL) was added slowly via a syringe, and the reaction was stirred for 3 hours during which the temperature did not rise above 5° C. After the solvent was removed on a rotary evaporator, pentane (600 mL) was added to the residue. The solid which separated was removed by filtration. Evaporation of solvent gave a light oil which was chromatographed on a silica gel column. The pure compound was eluted with pet ether to afford 1,1-dibromo-4-methyl-pent-1-ene 6 (16.5g,78%).

NMR (CDCl$_3$): δ 6.38 (triplet, 1H), 1.95 (triplet, 2H), 1.70 (m, 1H), and 0.89 (d, 6H).

Step 2: Synthesis of 5-Methyl-hex-2-ynoic acid ethyl ester 1,1-Dibromo-4-methyl-pent-1-ene 6 (40 g, 165.9 mmol) was dissolved in dry THF (120 mL) and cooled to −78° C. While stirring, n-butyllithium (1.6 M solution in hexane, 190.8 mL, 305 mmol) was added dropwise in a few minutes. After 1 hour, ethyl chloroformate (15 mL, 154.5 mmol) was added, and the reaction was stirred overnight during which it warmed to room temperature. It was poured onto water and extracted with ether (3×250 mL), dried on magnesium sulfate and evaporated. The light oil was flash chromatographed on a silica gel column, and the compound was eluted with 10% ether in pet ether to afford 5-methyl-hex-2-ynoic acid ethyl ester 7 (23.6 g, 92%).

NMR (CDCl$_3$): δ 4.14 (m, 2H), 2.16 (d, 2H), 1.85 (m, 1H), 1.24 (triplet, 3H), and 0.94 (d, 6H).

Step 3: Synthesis of (Z)-5-Methyl-hex-2-enoic acid ethyl ester

5-Methyl-hex-2-ynoic acid ethyl ester 7 (20.97 g) in THF (540 mL), pyridine (60 mL), and 5% Pd/BaSO$_4$ (1.10 g) was hydrogenated in 3.25 hours. The solvent was evaporated, and the light oil was chromatographed on a silica gel coulmn. After recovering some unreacted acetylene, the olefin was eluted with 5% ether in pet ether to give pure fractions of (Z)-5-methyl-hex-2-enoic acid ethyl ester 8 (12.0 g).

NMR (CDCl$_3$): δ 6.22 (m, 1H), 5.74 (d, 1H), 4.10 (m, 2H), 2.51 (triplet, 2H), 1.67 (m, 1H), 1.24 (triplet, 3H), and 1.16 (d, 6H).

N-Benzyl-N-(methoxymethyl) trimethylsilylmethylamine (Reagent for Step 4)

n-Butyllithium (1.6 M solution in hexane, 34.85 mL, 55.76 mmol) was added to N-benzyltrimethylsilylmethylamine (10 g, 55.76 mmol) in dry THF (140 mL) and stirred at −78° C. under nitrogen atmosphere. After 45 minutes, methoxymethyl chloride (4.3 mL, 55.76 mmol) in THF (6 mL) was added and then stirred for another 3 hours. The THF was evaporated, and the residue was dissolved in hexane, washed with water, and dried over sodium sulfate. The solvent was evaporated to give under reduced pressure to give N-benzyl-N-(methoxymethyl)trimethylsilylmethylamine (10 g).

Step 4: (cis)-1-Benzyl-4-isobutyl-pyrrolidine-3-carboxylic acid ethyl ester

N-Benzyl-N-(methoxymethyl)trimethylsilylmethylamine (4.0 g, 16.8 mmol), followed by TFA (1.0 M solution in CH$_2$Cl$_2$, 1.0 mL, 1 mmol) were added to a solution of (Z)-5-methyl-hex-2-enoic acid ethyl ester 8 (3.0 g, 19.2 mmol) in methylene chloride (30 mL) maintained at −5° C. under nitrogen atmosphere. After 15 minutes, the bath was removed and stirring was continued overnight. The reaction mixture was washed with saturated NaHCO$_3$ (10 mL), water (15 mL), brine (20 mL), and dried. The product was purified by chromatography on silica gel, and compound was eluted with 20% ethyl acetate in hexane to give (cis)-1-benzyl-4-isobutyl-pyrrolidine-3-carboxylic acid ethyl ester 9 as an oil (2.25 g, 41%).

Step 5: Synthesis of (cis)-4-Isobutyi-pyrrolidine-3-carboxylic acid (cis)-1-Benzyl-4-isobutyl-pyrrolidine-3-carboxylic acid ethyl ester 9 (2.25 g, 7.78 mmol) in ethanol (75 mL) and 20% Pd/C (210 mg) was hydrogenated for 5.5 hours. The reaction mixture was filtered through a pad of Celite, and the filtrate was concentrated to give [3R-(cis)]-4-isobutyl-pyrrolidine-3-carboxylic acid ethyl ester 10 as an oil. Proton NMR showed the absence of a benzyl group. To the 10 was added 6N HCl (20 mL), and the solution was refluxed overnight. After the solvent was evaporated at reduced pressure crude product was loaded onto a column of Dowax 50WX8-100 ion-exchange resin (30 g) which had been pre-washed to neutral (pH-7) with HPLC grade water. The resin was again washed to pH-7, followed by elution of the compound with 0.5N ammonium hydroxide solution. The solvent was evaporated, and the product was crystallized from methanol-ether to give (cis)-4-isobutyl-pyrrolidine-3-carboxylic acid 11 (470 mg). Analysis by tlc (8% $NH_4OH$ in 95% ethanol, visualized with ninhydrin) indicated the presence of minor fast chromatographic spot (trans-isomer). The mixture was adsorbed onto silica get and chromatographed on a Biotage Flash system. Compound was eluted with 5% $NH_4OH$ in 95% ethanol. After evaporation of solvent, the product was converted to the HCl salt and reprocessed on ion-exchange column, followed by crystalization from methanol-ether to give (cis)-4-isobutyl-pyrrolidine-3-carboxylic acid 11 (320 mg).

$^1$H NMR (400 MHz, $CD_3OD$): δ 3.46 (dd, 1H), 3.31 (dd, 1H), 3.18 (dd, 1H), 3.15 (m, 1H), 2.49 (m, 1H), 1.63 (m, 1H), 1.47 (m, 1H), 1.25 (m, 1H), and 0.88 (6H). Anal. Calcd for $C_9H_{17}NO_2$: C, 63.13; H, 10.01; N, 8.18. Found: C, 62.86; H, 9.82; N, 8.05.

EXAMPLE 2

[trans]-4-Isobutyl-pyrrolidine-3-carboxylic acid (See Scheme 4)

Step 1: (E)-5-Methyl-hex-2-enoic acid ester

Sodium hydride (60% dispersion in oil) (3.87 g, 96.7 mmol) was washed with pentane and stirred in dimethoxyethane (80 mL). While cooling in ice bath, a solution of triethyl phosphonoacetate (21.7 g, 96.7 mmol) was added slowly in 15 minutes. The reaction was stirred for additional 15 minutes and isovaleraldehyde 1 (31 mL, 290 mmol) in dimethoxyethane (20 mL) was added in one portion. It was refluxed overnight, concentrated, and hexane/water (500 mL, 3/2v/v) was added. The organic portion was separated, washed with water (200 mL), brine (2×200 mL) and dried on magnesium sulfate. Evaporation of solvent gave an oil which was purified by flash chromatography on silica gel. The compound was eluted with 30% methylene chloride in pet ether to give (E)-5-methyl-hex-2-enoic acid ester 2 as a clear liquid (13.2 g).

NMR ($CDCl_3$): δ 6.89 (m, 1H), 5.75 (d, 1H), 4.14 (m, 2H), 2.05 (m, 2H), 1.69 (m, 1H), 1.25 (triplet, 3H), and 0.88 (d, 6H).

Step 2: Synthesis of [trans]-1-Benzyl-4-isobutyl-pyrrolidine-3-carboxylic acid ethyl ester N-Benzyl-N-(methoxymethyl)trimethylsilylmethylamine (2.84 g, 12 mmol), followed by TFA (1.0 M solution in $CH_2Cl_2$, 1.0 mL, 1 mmol) were added to a solution of (E)-5-methyl-hex-2-enoic acid ethyl ester (1.56 g, 10.0 mmol) in methylene chloride (30 mL) maintained at −5° C. under nitrogen atmosphere. After 15 minutes, the bath was removed and stirring was continued overnight. Saturated sodium bicarbonate was added, and the organic portion was separated, washed with brine, and dried. The product was purified by chromatography on silica gel, and compound was eluted with 20% ethyl acetate in hexane to give (trans)-1-Benzyl-4-isobutyl-pyrrolidine-3-carboxylic acid ethyl ester 3 as an oil (1.28 g, 44%).

NMR ($CDCl_3$): δ 7.28 (m, 5H), 4.09 (m, 2H), 3.56 (q, 2H), 2.81 (m, 2H), 2.69 (triplet, 1H), 2.51 (m, 2H), 2.18 (triplet, 1H), 1.51 (m, 1H), 1.38 (m, 1H), 1.27 (m, 1H), 1.20 (triplet, 3H), and 0.83 (d, 6H).

Step 3: [trans]-4-Isobutyl-pyrrolidine-3-carboxylic acid (trans)-1-Benzyl-4-isobutyl-pyrrolidine-3-carboxylic acid ethyl ester 3 (1.28 g, 4.42 mmol) in ethanol (75 mL) and 20% Pd/C (210 mg) was hydrogenated for 5.5 hours. The reaction mixture was filtered through a pad of Celite, and the filtrate was concentrated to give [3R-(trans)]-4-isobutyl-pyrrolidine-3-carboxylic acid ethyl ester 4 as an oil. Proton NMR ($CDCl_3$): δ 4.13 (m, 2H), 3.18 (m, 1H), 3.15 (m, 1H), 3.08 (m, 1H), 2.67 (brs, 1H), 2.46 (m, 2H), 2.34 (m, 1H), 1.55 (m, 1H), 1.37 (m, 1H), 1.25 (triplet, 3H) and 0.87 (q, 6H) showed the absence of a benzyl group. To the residue was added 6N HCl (20 mL), and the solution was refluxed overnight. After the solvent was evaporated at reduced pressure, crude product was loaded onto a column of Dowax 50WX8-100 ion-exchange resin (28 g) which had been pre-washed to neutral (pH-7) with hplc grade water. The resin was again washed to pH-7, followed by elution of the compound with 0.5N ammonium hydroxide solution. The fractions were monitored by tic (8% $NH_4OH$ in 95% ethanol, visualized with ninhydrin). The solvent was evaporated and the compound crystallized from methanol-ether to give (trans)-4-isobutyl-pyrrolidine-3-carboxylic acid 5 (280 mg). $^1$H NMR (400 MHz, $CD_3OD$): δ 3.44 (dd, 1H), 3.37 (d, 2H), 2.78 (dd, 1H), 2.52 (m, 2H), 1.60 (m, 1H), 1.51 (m, 1H), 1.26 (m, 1H), 0.89 (6H).

Anal. Calcd. for $C_9H_{17}NO_2$: C, 63.13; H, 10.01; N, 8.18. Found: C, 62.79; H, 9.45; N, 8.02.

General Procedure for the Preparation of 1-Benzyl-4-alkylpyrrolidine-3-carboxylic acid ethyl ester 2a–2h To a stirred solution of α,β-unsaturated carboxylic acid ethyl ester 1a–1h (11.70 mmol) in toluene (20 mL) was added N-benzyl-N-(methoxymethyl) trimethylsilylmethylamine (3.33 g, 14.10 mmol) at 0° C. under $N_2$. After 20 minutes, a solution of TFA (1 M in $CH_2Cl_2$, 1.17 mmol) was added slowly at 0° C. The mixture was stirred at 0° C. for 30 minutes and then at 22° C. for an additional 12 hours. The reaction was quenched with $H_2O$, extracted with $CHCl_3$, then dried over $MgSO_4$. The solvent was evaporated to dryness, and the oily residue was subjected to column chromatography (silica gel, hexanes:ether=6:1) to give 2a–2h as a colorless oil.

trans-1-Benzyl-4-methylpyrrolidine-3-carboxylic acid ethyl ester (2a). yield 100%; $^1$H NMR ($CDCl_3$): δ 1.07 (d, J=6.6 Hz, 3 H, $CH_3$), 1.18 (t, J=7.1 Hz, 3 H, $CH_2C\underline{H}_3$), 2.13–2.17 (m, 1 H, pyrrolidine ring), 2.40–2.50 (m, 2 H, pyrrolidine ring), 2.68–2.82 (m, 3 H, pyrrolidine ring), 3.48–3.59 (ABq, J=32.9 Hz, 2 H, $CH_2Ph$), 4.04–4.09 (q, J=7.1 Hz, 2 H, C$\underline{H}_2CH_3$), 7.17–7.25 (m, 5 H, aromatic ring); $^{13}$C($CDCl_3$): δ 14.24, 19.74, 36.78, 50.65, 56.64, 60.09, 60.44, 61.63, 126.87, 128.19, 128.66,138.98, 174.67; MS (CI) m/z 248 (M+1)$^+$. Anal. ($C_{15}H_{21}NO_2$) C, H, N.

1-Benzyl-4,4-dimethylpyrrolidine-3-carboxylic acid ethyl ester (2b). yield 28%; $^1$H NMR ($CDCl_3$): δ 0.93 (s, 3 H, $CH_3$), 1.17 (s, 3 H, $CH_3$), 1.17–1.21 (t, J=7.0 Hz, 3 H, $CH_2C\underline{H}_3$), 2.20–2.87 (m, 5 H, pyrrolidine ring), 3.50–3.59 (ABq, J=26.2 Hz, 2 H, $CH_2Ph$), 4.03–4.14 (m, 2 H, C$\underline{H}_2CH_3$), 7.13–7.30 (m, 5 H, aromatic ring); $^{13}$C($CDCl_3$): δ 14.41, 24.15, 29.59, 41.49, 53.45, 55.84, 60.14, 60.18, 68.14, 126.82, 128.20, 128.55, 139.41, 173.33; MS (CI) m/z 262 (M+1)$^+$. Anal. ($C_{16}H_{23}NO_2$) C, H, N.

trans-1-Benzyl-4-ethylpyrrolidine-3-carboxylic acid ethyl ester (2c). yield 95%; $^1$H NMR (CDCl$_3$): δ 0.86 (t, J=7.3 Hz, 3 H, CH$_2$C$\underline{H}_3$), 1.21 (t, J=7.1 Hz, 3 H, OCH$_2$C$\underline{H}_3$), 1.37–1.57 (m, 2 H, C$\underline{H}_2$CH$_3$), 2.22–2.79 (m, 5 H, pyrrolidine ring), 3.51–3.64 (ABq, J=39.3 Hz, 2 H, CH$_2$Ph), 4.08–4.13 (m, 2 H, OC$\underline{H}_2$CH$_3$), 7.23–7.29 (m, 5 H, aromatic ring); $^{13}$C(CDCl$_3$): δ 12.46, 14.25, 28.05, 43.73, 48.97, 56.84, 59.72, 60.07, 60.49, 126.89, 128.21, 128.64, 139.02, 175.01; MS (CI) m/z 262 (M+1)$^+$. Anal. ($C_{16}H_{23}NO_2$) C, H, N.

trans-1-Benzyl-4-isopropylpyrrolidine-3-carboxylic acid ethyl ester (2d). yield 79%; $^1$H NMR (CDCl$_3$): δ 0.84–0.88 (m, 6 H, CH$_3$, CH$_3$), 1.20–1.22 (t, J=8.0 Hz, 3 H, CH$_2$C$\underline{H}_3$), 1.54–1.62 (m, 1 H, C$\underline{H}$(CH$_3$)$_2$), 2.24–2.32 (m, 2 H, pyrrolidine ring), 2.63–2.69 (m, 2 H, pyrrolidine ring), 2.74–2.80 (m, 2 H, pyrrolidine ring), 3.47–3.65 (ABq, J=56.4 Hz, 2 H, CH$_2$Ph), 4.06–4.14 (m, 2 H, C$\underline{H}_2$CH$_3$), 7.19–7.30 (m, 5 H, aromatic ring); $^{13}$C(CDCl$_3$): δ 14.19, 20.59, 20.81, 32.20, 47.16, 48.67, 57.56, 58.23, 59.99, 60.45, 126.82, 128.17, 128.54, 139.05, 175.33; MS (CI) m/z 276 (M+1)$^+$. Anal. ($C_{17}H_{25}NO_2$) C, H, N.

trans-1-Benzyl-4-propylpyrrolidine-3-carboxylic acid ethyl ester (2e). yield 72%; $^1$H NMR (CDCl$_3$): δ 0.84–0.88 (t, J=7.1 Hz, 3 H, CH$_2$CH$_2$C$\underline{H}_3$), 1.20–1.24 (t, J=7.1 Hz, 3 H, CH$_2$C$\underline{H}_3$), 1.26–1.54 (m, 4 H, C$\underline{H}_2$C$\underline{H}_2$CH$_3$), 2.21–2.82 (m, 6 H, pyrrolidine ring), 3.51–3.64 (ABq, J=40.6 Hz, 2 H, CH$_2$Ph), 4.07–4.16 (m, 2 H, C$\underline{H}_2$CH$_3$), 7.19–7.31 (m, 5 H, aromatic ring); $^{13}$C(CDCl$_3$): δ 14.09, 14.22, 21.13, 37.51, 41.74, 49.25, 56.75, 59.98, 60.05, 60.43, 126.84, 128.18, 128.61, 139.01, 174.95; MS (CI) m/z 276 (M+1)$^+$. Anal. ($C_{17}H_{25}NO_2$) C, H, N.

trans-1-Benzyl-4-isobutylpyrrolidine-3-carboxylic acid ethyl ester (2f). yield 99%; $^1$H NMR (CDCl$_3$): δ 0.83–0.88 (d, J=7.1 Hz, 6 H, CH(C$\underline{H}_3$)$_2$), 1.20–1.24 (t, J=7.1 Hz, 3 H, CH$_2$C$\underline{H}_3$), 1.27–1.51(m, 3 H, C$\underline{H}_2$C$\underline{H}$(CH$_3$)$_2$), 2.18–2.81 (m, 6 H, pyrrolidine ring), 3.50–3.65 (ABq, J=43.4 Hz, 2 H, CH$_2$Ph), 4.07–4.15 (m, 2 H, C$\underline{H}_2$CH$_3$), 7.21–7.30 (m, 5 H, aromatic ring); $^{13}$C(CDCl$_3$): δ 14.22, 22.42, 22.92, 26.46, 39.89, 44.84, 49.48, 56.65, 60.07, 60.33, 60.44, 126.87, 128.19, 128.63, 138.95, 174.93; MS (CI) m/z 290 (M+1)$^+$. Anal. ($C_{18}H_{27}NO_2$) C, H, N.

trans-1-Benzyl-4-butylpyrrolidine-3-carboxylic acid ethyl ester (2f). yield 82%; $^1$H NMR (CDCl$_3$): δ 0.85 (t, J=7.1 Hz, 3 H, CH$_2$CH$_2$C$\underline{H}_3$), 1.20–1.24 (t, J=7.1 Hz, 3 H, CH$_2$C$\underline{H}_3$), 1.27–1.51 (m, 3 H, C$\underline{H}_2$C$\underline{H}$(CH$_3$)$_2$), 3.50–3.65 (ABq, J=43.4 Hz, 2 H, CH$_2$Ph), 4.07–4.15 (m, 2 H, C$\underline{H}_2$CH$_3$), 7.20–7.30 (m, 5 H, aromatic ring); $^{13}$C(CDCl$_3$): δ 13.98, 14.22, 19.18, 22.67, 30.19, 34.93, 41.95, 49.27, 56.75, 60.06, 60.44, 126.84, 128.18, 128.62, 139.00, 174.95; MS (CI) m/z 290 (M+1)$^+$. Anal. ($C_{18}H_{27}NO_2$) C, H, N.

General Procedure for the Preparation of 4-Alkylpyrrolidine-3-carboxylic acid 3a–3h. (Scheme 5)

To a solution of 1-benzyl-4-alkylpyrrolidine-3-carboxylic acid ethyl ester 2a–2h (4.42 mmol) in ethanol (75 mL) was added 20% Pd/C (0.21 g) and hydrogenated at 50 psi for 11 hours. The reaction mixture was filtered through a pad of celite. The filtrate was concentrated to give 4-alkylpyrrolidine-3-carboxylic acid ethyl ester as an oil. To the crude oil was added 3N HCl (20 mL). The reaction mixture was refluxed for 12 hours. After the solvent was evaporated at reduced pressure, the crude product was subjected to ion exchange column (Dowex 50) and recrystallized from methanol-ether to give 4-alkylpyrrolidine-3-carboxylic acid 3a–3h as a white solid.

trans-4-Methylpyrrolidine-3-carboxylic acid (3a). yield 90%; mp 208–210° C.; $^1$H NMR (CD$_3$OD): δ 1.14 (d, J=6.3 Hz, 3 H, CH$_3$), 2.42–2.54 (m, 2 H, pyrrolidine ring), 2.74–2.79 (m, 1 H, pyrrolidine ring), 3.71–3.46 (m, 3 H, pyrrolidine ring); $^{13}$C(CD$_3$OD): δ 15.77, 37.72, 48.33, 51.34, 52.75, 177.16; MS (CI) m/z 130 (M+1)$^+$. Anal. ($C_6H_{11}NO_2$) C, H, N.

trans-4,4-Dimethylpyrrolidine-3-carboxylic acid (3b). yield 84%; mp 282–286° C.; $^1$H NMR (CD$_3$OD): δ 1.11 (s, 3 H, CH$_3$), 1.21 (s, 3 H, CH$_3$), 2.59–2.63 (m, 1 H, pyrrolidine ring), 2.94 (d, J=11.3 Hz, 1 H, pyrrolidine ring), 3.15 (d, J=11.3 Hz, 1 H, pyrrolidine ring), 3.36–3.41 (m, 1 H, pyrrolidine ring), 3.53–3.58 (m, 1 H, pyrrolidine ring); $^{13}$C(CD$_3$OD): δ 21.33, 25.87, 41.05, 48.21, 55.51, 56.50, 177.10; MS (CI) m/z 144 (M+1)$^+$. Anal. ($C_7H_{13}NO_2$) C, H, N.

trans-4-Ethylpyrrolidine-3-carboxylic acid (3c). yield 78%; mp 197–199° C.; $^1$H NMR (CD$_3$OD): δ 0.98 (m, 3 H, CH$_3$), 1.41–1.44 (m, 1 H, C$\underline{H}_2$CH$_3$), 1.65–1.70 (m, 1 H, C$\underline{H}_2$CH$_3$), 2.34–2.39 (m, 1 H, pyrrolidine ring), 2.56–2.62 (m, 1 H, pyrrolidine ring), 2.80–2.88 (m, 1 H, pyrrolidine ring), 3.36–3.48 (m, 3 H, pyrrolidine ring); $^{13}$C(CD$_3$OD): δ 11.10, 25.35, 44.47, 48.46, 49.65, 51.07, 177.60; MS (CI) m/z 144 (M+1)$^+$. Anal. ($C_7H_{13}NO_2$) C, H, N.

trans-4-Isopropylpyrrolidine-3-carboxylic acid (3d). yield 88%; mp 243–245° C.; $^1$H NMR (CD$_3$OD): δ 0.92 (d, J=6.5 Hz, 3 H, CH$_3$), 0.99 (d, J=6.5 Hz, 3 H, CH$_3$), 1.67–1.72 (m, 1 H, C$\underline{H}$(CH$_3$)$_2$), 2.29–2.37 (m, 1 H, pyrrolidine ring), 2.66–2.72 (m, 1 H, pyrrolidine ring), 2.89–2.94 (m, 1 H, pyrrolidine ring), 3.31–3.45 (m, 3 H, pyrrolidine ring); $^{13}$C(CD$_3$OD): δ 19.00, 19.94, 30.32, 48.22, 49.20, 49.26, 49.40, 178.18; MS (CI) m/z 158 (M+1)$^+$. Anal. ($C_8H_{15}NO_2$) C, H, N.

trans-4-Propylpyrrolidine-3-carboxylic acid (3e). yield 88%; mp 223–226° C.; $^1$H NMR (CD$_3$OD): δ 0.92 (t, J 6.6 Hz, 3 H, CH$_3$), 1.32–1.40 (m, 3 H, C$\underline{H}_2$C$\underline{H}_2$), 1.61 (m, 1 H, C$\underline{H}_2$CH$_2$), 2.42–2.46 (m, 1 H, pyrrolidine ring), 2.55–2.60 (q, J=7.5 Hz, 1 H, pyrrolidine ring), 2.80–2.85 (t, J=11.3 Hz, 1 H, pyrrolidine ring), 3.38–3.47 (m, 3 H, pyrrolidine ring); $^{13}$C(CD$_3$OD): δ 12.96, 20.69, 34.68, 42.62, 48.45, 49.94, 51.43, 177.51; MS (CI) m/z 158 (M+1)$^+$. Anal. ($C_8H_{15}NO_2$) C, H, N.

trans-4-Isobutylpyrrolidine-3-carboxylic acid (3f). yield 86%; mp 255–257° C.; $^1$H NMR (CD$_3$OD): δ 0.89 (m, 6 H, CH$_3$), 1.26 (m, 1 H, CH$_2$C$\underline{H}$(CH$_3$)$_2$), 1.51 (m, 1 H, C$\underline{H}_2$CH(CH$_3$)$_2$), 1.60 (m, 1 H, C$\underline{H}_2$CH(CH$_3$)$_2$), 2.52 (m, 2 H, pyrrolidine ring), 2.78 (m, 1 H, pyrrolidine ring), 3.37 (m, 2 H, pyrrolidine ring), 3.44 (m, 1 H, pyrrolidine ring); $^{13}$C (CD$_3$OD): δ 21.07, 22.07, 26.29, 40.81, 41.83, 48.39, 50.11, 51.78, 177.47; MS (CI) m/z 172 (M+1)$^+$. Anal. ($C_9H_{17}NO_2$) C,H,N.

cis-4-Isobutylpyrrolidine-3-carboxylic acid (3g). yield 85%; mp 260–262° C.; $^1$H NMR (CD$_3$OD): δ 0.88 (m, 6 H, CH$_3$), 1.25 (m, 1 H, CH$_2$C$\underline{H}$(CH$_3$)$_2$), 1.47 (m, 1 H, C$\underline{H}_2$CH(CH$_3$)$_2$), 1.63 (m, 1 H, C$\underline{H}_2$CH(CH$_3$)$_2$), 2.49 (m, 1 H, pyrrolidine ring), 3.15 (m, 1 H, pyrrolidine ring), 3.18 (m, 1 H, pyrrolidine ring), 3.31–3.46 (m, 3 H, pyrrolidine ring; MS (CI) m/z 172 (M+1)$^+$. Anal. ($C_9H_{17}NO_2$) C, H, N.

trans-4-Butylpyrrolidine-3-carboxylic acid (3h). yield 85%; mp 234–237° C.; $^1$H NMR (CD$_3$OD): δ 0.89 (m, 3 H, CH$_3$), 1.33 (m, 5 H, C$\underline{H}_2$C$\underline{H}_2$C$\underline{H}_2$), 1.65 (m, 1 H, C$\underline{H}_2$CH$_2$CH$_2$), 2.38–2.43 (m, 1 H, pyrrolidine ring), 2.55–2.60 (q, J=7.5 Hz, 1 H, pyrrolidine ring), 2.80–2.85 (t, J=8.8 Hz, 1 H, pyrrolidine ring), 3.28–3.48 (m, 3 H, pyrrolidine ring); $^{13}$C (CD$_3$OD): δ 12.85, 22.33, 29.77, 32.20, 42.83, 48.39, 49.91, 51.43, 177.62; MS (CI) m/z 172 (M+1)$^+$. Anal. (C$_9$H$_{17}$NO$_2$) C, H, N.

3-[(E)-3-Isobutylpropenoyl]-4-(S)-phenyl-2-oxazolidinone (7a). (Scheme 6)

To a solution of (E)-5-methyl-hex-2-enoic acid (3.2 g, 25 mmol) in toluene (20 mL) was added oxalyl chloride (4.4 mL, 50 mmol) slowly at 0° C. under N$_2$ followed by one drop of DMF. The mixture was stirred at 22° C. for 1 hour. The volatiles were removed under reduced pressure to give the desired acid chloride which was used without further purification. To a solution of NaH (0.84 g, 21 mmol) in THF (30 mL) was added a solution of (S)-(–)-4-phenyl-2-oxazolidinone (3.4 g, 21 mmol) in THF (10 mL) at 0° C. The mixture was stirred at 22° C. for 1 hour. The crude acid chloride was then introduced while maintaining the temperature at 0° C. The mixture was stirred at 0° C. for 1 hour and then at 22° C. for an additional 12 hours. The reaction was quenched with 1N HCl aqueous solution, extracted with CHCl$_3$, then dried over Na$_2$SO$_4$. After the solvent was evaporated at reduced pressure, the crude product was subjected to column chromatography (silica gel, hexanes:ether=2:1) to give 6.25 g (100% yield) of 7a as a white solid. mp 84–85° C.; $^1$H NMR (CDCl$_3$): δ 0.81 (d, J=6.8 Hz, 6 H, CH(CH$_3$)$_2$), 1.68–1.78 (m, 1 H, CH$_2$CH(CH$_3$)$_2$), 2.11–2.14 (m, 2 H, CH$_2$CH(CH$_3$)$_2$), 4.24–4.27 (m, 1 H, oxazolidinone ring), 4.65–4.72 (t, J=8.8 Hz, 1 H, oxazolidinone ring), 5.44–5.48 (m, 1 H, oxazolidinone ring), 7.02–7.09 (m, 1 H, vinyl), 7.23–7.28 (m, 1 H, vinyl), 7.31–7.38 (m, 5 H, aromatic); $^{13}$C(CDCl$_3$): δ 22.35, 22.39, 27.88, 41.82, 57.77, 69.92, 121.11, 125.95, 128.63, 129.16, 139.14, 151.10, 153.70, 164.56; MS (CI) m/z 274 (M+1)$^+$. Anal. (C$_{16}$H$_{19}$NO$_3$) C, H, N.

1-Benzyl-4-(R)-isobutyl-3-(R)-[4'-(S)-phenyl-2'-oxazolidinon-3'-yl]carbonyl]pyrrolidine (8a). (Scheme 6)

To a stirred solution of 3-[(E)-3-isobutylpropenoyl]-4-(S)-phenyl-2-oxazolidinone (1.50 g, 5.50 mmol) in toluene (20 mL) was added N-benzyl-N-(methoxymethyl) trimethylsilylmethylamine (1.56 g, 6.60 mmol) at 0° C. under N$_2$. After 20 minutes, a solution of TEA (1 M in CH$_2$Cl$_2$, 0.55 mmol) was added slowly at 0C. The mixture was stirred at 0° C. for 30 minutes and then at 22° C. for an additional 12 hours. The reaction was quenched with H$_2$O, extracted with CHCl$_3$, then dried over MgSO$_4$. The solvent was evaporated to dryness, and the oily residue was subjected to column chromatography (silica gel, hexanes:ether2:1) to give 1.37 g (62% yield) of 8a as a white solid. $^1$H NMR (CDCl$_3$): δ 0.84–0.86 (m, 6 H, CH(CH$_3$)$_2$), 1.26–1.29 (m, 2 H, CH$_2$CH(CH$_3$)$_2$), 1.42–1.47 (m, 1 H, CH$_2$CH(CH$_3$)$_2$), 2.08 (t, J=7.3 Hz, 1 H, pyrrolidine ring), 2.62 (dd, J=9.8 Hz, 4.6 Hz, 1 H, pyrrolidine ring), 2.83–2.94 (m, 3 H, pyrrolidine ring), 3.37–3.67 (ABq, 2 H, CH$_2$Ph), 3.68–3.72 (m, 1 H, pyrrolidine ring), 4.16–4.19 (m, 1 H, oxazolidinone ring), 4.63 (t, J=9.0 Hz, 1 H, oxazolidinone ring), 5.40 (m, 1 H, oxazolidinone ring), 7.18–7.36 (m, 5 H, aromatic); $^{13}$C(CDCl$_3$): δ 22.46, 23.05, 26.72, 37.00, 44.07, 49.41, 57.48, 57.85, 59.84, 60.54, 69.87, 125.67, 126.80, 128.21, 128.48, 128.65, 129.25, 139.01, 139.05, 153.55, 173.71; MS (CI) m/z 407 (M+1)$^+$. Anal. (C$_{25}$H$_{30}$N$_2$O$_3$) C, H, N.

trans-4-(R)-Isobutylpyrrolidine-3-(R)-carboxylic acid (10a). (Scheme 6)

To a solution of 1-benzyl-4-(R)-isobutyl-3-(R)-[4'-(S)-phenyl-2'-oxazolidinon-3'-yl)carbonyl]pyrrolidine (1.37 g, 3.37 mmol) in THF (30 mL)was added a solution of LiOH (1 M in H$_2$O, 8.44 mmol) and H$_2$O$_2$ (30%, 6.75 mmol) in H$_2$O (10 mL) at 0° C. slowly. The reaction mixture was stirred at 0° C. for 1 hour, then diluted with water (40 mL). Sodium sulfite (0.85 g, 6.75 mmol) was added, and the mixture was extracted with ethyl acetate. The aqueous phase was adjusted to pH 5.0 with KH$_2$PO$_4$ (1.51 g, 11.1 mmol) and 10% HCl. This solution was extracted with isopropyl alcohol:methylene chloride (1:3), which was dried over Na$_2$SO$_4$ and concentrated to afford 0.88 g of 1-benzyl-4-(R)-isobutylpyrrolidine-3-(R)-carboxylic acid which was used without further purification. To a solution of this carboxylic acid (0.72 g) in ethanol (55 mL) was added 20% Pd/C (0.11 g) and hydrogenated at 50 psi for 11 hours. The reaction mixture was filtered through a pad of celite. After the solvent was evaporated at reduced pressure, the crude product was subjected to ion exchange column (Dowex 50) and recrystallized from methanol-ether to give 0.33 g (71% yield) of 10a as a white solid. [α]$_D$=+44.8°; mp 236–239° C.; $^1$H NMR (CD$_3$OD): δ 0.89 (m, 6 H, CH$_3$), 1.26 (m, 1 H, CH$_2$CH(CH$_3$)$_2$), 1.51 (m, 1 H, CH$_2$CH(CH$_3$)$_2$), 1.60 (m, 1 H, CH$_2$CH(CH$_3$)$_2$), 2.52 (m, 2 H, pyrrolidine ring), 2.78 (m, 1 H, pyrrolidine ring), 3.37 (m, 2 H, pyrrolidine ring), 3.44 (m, 1 H, pyrrolidine ring); $^{13}$C(CD$_3$OD): δ 21.07, 22.07, 26.29, 40.81, 41.83, 48.39, 50.11, 51.78, 177.47; MS (CI) m/z 172 (M+1)$^+$. Anal. (C$_9$H$_{17}$NO$_2$) C, H, N.

3-[(E)-3-Isobutylpropenoyl]-4-(R)-phenyl-2-oxazolidinone (7b). (Scheme 6)

To a solution of (E)-5-methyl-hex-2-enoic acid (1.77 g, 13.8 mmol) in toluene (20 mL) was added oxalyl chloride (2.4 mL, 27.6 mmol) slowly at 0° C. under N$_2$ followed by one drop of DMF. The mixture was stirred at 22° C. for 1 hour. The volatiles were removed under reduced pressure to give the desired acid chloride which was used without further purification. To a solution of NaH (0.37 g, 9.2 mmol) in THF (30 mL) was added a solution of (R)-(–)-4-phenyl-2-oxazolidinone (1.5 g, 9.2 nmmol) in THF (10 mL) at 0° C. The mixture was stirred at 22° C. for 1 hour. The crude acid chloride was then introduced while maintaining the temperature at 0° C. The mixture was stirred at 0° C. for 1 hour and then at 22° C. for an additional 12 hours. The reaction was quenched with 1N HCl aqueous solution, extracted with CHCl$_3$, then dried over Na$_2$SO$_4$. After the solvent was evaporated at reduced pressure, the crude product was subjected to column chromatography (silica gel, hexanes:acetone=3:1) to give 2.5 g (100% yield) of 7b as a white solid. mp 84–85° C.; $^1$H NMR (CDCl$_3$): δ 0.81 (d, J=6.8 Hz, 6 H, CH(CH$_3$)$_2$), 1.68–1.78 (mn, 1 H, CH$_2$CH(CH$_3$)$_2$), 2.11–2.14 (m, 2 H, CH$_2$CH(CH$_3$)$_2$), 4.24–4.27 (m, 1 H, oxazolidinone ring), 4.65–4.72 (t, J=8.8 Hz, 1 H, oxazolidinone ring), 5.44–5.48 (m, 1 H, oxazolidinone ring), 7.02–7.09 (m, 1 H, vinyl), 7.23–7.28 (m, 1 H, vinyl), 7.31–7.38 (m, 5 H, aromatic); $^{13}$C(CDCl$_3$): δ 22.35, 22.39, 27.88, 41.82, 57.77, 69.92, 121.11, 125.95, 128.63, 129.16, 139.14, 151.10, 153.70, 164.56; MS (CI) m/z 274 (M+1)$^+$. Anal. (C$_{16}$H$_{19}$NO$_3$) C,H, N.

1-Benzyl-4-(S)-isobutyl-3-(S)-[4'-(R)-phenyl-2'-oxazolidinon-3'-yl]carbonyl]pyrrolidine (8b).

To a stirred solution of 3-[(E)-3-isobutylpropenoyl]-4-(R)-phenyl-2-oxazolidinone (1.50 g, 5.50 mmol) in toluene (20 mL) was added N-benzyl-N-(methoxymethyl) trimethylsilylmethylamine (1.56 g, 6.60 mmol) at 0° C. under N$_2$. After 20 minutes, a solution of TFA (1 M in CH$_2$Cl$_2$, 0.55 mmol) was added slowly at 0° C. The mixture was stirred at 0° C. for 30 minutes and then at 22° C. for an additional 12 hours. The reaction was quenched with $H_2O$, extracted with $CHCl_3$, then dried over $MgSO_4$. The solvent was evaporated to dryness, and the oily residue was subjected to column chromatography (silica gel, hexanes:ether=2:1) to give 1.45 g (65% yield) of 8b as a white solid. $^1$H NMR ($CDCl_3$): δ 0.84–0.86 (m, 6 H, CH(C$\underline{H}_3$)$_2$), 1.26–1.29 (m, 2 H, C$\underline{H}_2$CH(CH$_3$)$_2$), 1.42–1.47 (m, 1 H, CH$_2$C$\underline{H}$(CH$_3$)$_2$), 2.08 (t, J=7.3 Hz, 1 H, pyrrolidine ring), 2.62 (dd, J=9.8 Hz, 4.6 Hz, 1 H, pyrrolidine ring), 2.83–2.94 (m, 3 H, pyrrolidine ring), 3.37–3.67 (ABq, 2 H, CH$_2$Ph), 3.68–3.72 (m, 1 H, pyrrolidine ring), 4.16–4.19 (m, 1 H, oxazolidinone ring), 4.63 (t, J=9.0 Hz, 1 H, oxazolidinone ring), 5.40 (m, 1 H, oxazolidinone ring), 7.18–7.36 (m, 5 H, aromatic); $^{13}$C(CDCl$_3$): δ 22.46, 23.05, 26.72, 37.00, 44.07, 49.41, 57.48, 57.85, 59.84, 60.54, 69.87, 125.67, 126.80, 128.21, 128.48, 128.65, 129.25, 139.01, 139.05, 153.55, 173.71; MS (CI) m/z 407 (M+1)$^+$. Anal. ($C_{25}H_{30}N_2O_3$) C, H, N.

trans-4-(S)-Isobutylpyrrolidine-3-(S)-carboxylic acid (10b). (Scheme 6)

To a solution of 1-benzyl-4-(S)-isobutyl-3-(S)-[4'-(R)-phenyl-2'-oxazolidinon-3'-yl)carbonyl]pyrrolidine (1.44 g, 3.56 mmol) in THF (30 mL)was added a solution of LiOH (1 M in H$_2$O, 8.89 mmol) and H$_2$O$_2$ (30%, 7.11 mmol) in H$_2$O(10 mL) at 0° C. slowly. The reaction mixture was stirred at 0° C. for 1 hour, then diluted with water (40 mL). Sodium sulfite (0.89 g, 7.11 mmol) was added, and the mixture was extracted with ethyl acetate. The aqueous phase was adjusted to pH 5.0 with KH$_2$PO$_4$ (1.59 g, 11.7 mmol) and 10% HCl. This solution was extracted with isopropyl alcohol:methylene chloride (1:3), which was dried over Na$_2$SO$_4$ and concentrated to afford 0.93 g of 1-benzyl-4-(S)-isobutylpyrrolidine-3-(S)-carboxylic acid which was used without further purification. To a solution of this carboxylic acid (0.94 g) in ethanol (55 mL) was added 20% Pd/C (0.21 g) and hydrogenated at 50 psi for 11 hours. The reaction mixture was filtered through a pad of celite. After the solvent was evaporated at reduced pressure, the crude product was subjected to ion exchange column (Dowex 50) and recrystallized from methanol-ether to give 0.43 g (70% yield) of 10b as a white solid. [α]$_D$=−45.8°; mp 251–254° C.; $^1$H NMR (CD$_3$OD): δ 0.89 (m, 6 H, CH$_3$), 1.26 (m, 1 H, CH$_2$C$\underline{H}$(CH$_3$)$_2$), 1.51 (m, 1 H, C$\underline{H}_2$CH(CH$_3$)$_2$), 1.60 (m, 1 H, C$\underline{H}_2$CH(CH$_3$)$_2$), 2.52 (m, 2 H, pyrrolidine ring), 2.78 (m, 1 H, pyrrolidine ring), 3.37 (m, 2 H, pyrrolidine ring), 3.44 (m, 1 H, pyrrolidine ring); $^{13}$C(CD$_3$OD): δ 21.07, 22.07, 26.29, 40.81, 41.83, 48.39, 50.11, 51.78, 177.47; MS (CI) m/z 172 (M+1)$^+$. Anal. (C$_9$H$_{17}$NO$_2$) C, H, N.

What is claimed is:

1. A compound of formula I

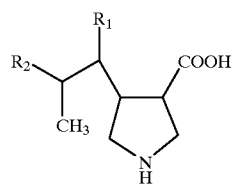

I or a pharmaceutically acceptable salt thereof or a prodrug thereof wherein

R$_1$ is hydrogen or a straight or branched alkyl of from 1 to 5 carbons;

R$_2$ is a straight or branched alkyl of from 1 to 5 carbons; and

R$_1$ and R$_2$ when taken together form a carbocyclic ring of from 3 to 7 atoms.

2. A compound according to claim 1 wherein
R$_1$ is H, methyl, or ethyl; and
R$_2$ is methyl or ethyl.

3. A compound according to claim 1 and selected from (cis)-4-isobutyl-pyrrolidine-3-carboxylic acid and (trans)-4-isobutyl-pyrrolidine-3-carboxylic acid.

4. A compound according to claim 1 wherein R$_1$ and R$_2$ are taken to form a carbocyclic ring of from 3 to 7 atoms.

5. A compound according to claim 1 and selected from where R$_1$ and R$_2$ form a five or six membered ring.

6. A compound of Formula I

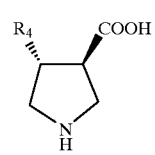

IA or a pharmaceutically acceptable salt thereof wherein R$_4$ is a alkyl of 3 or 4 carbons.

7. A compound according to claim 6 and selected from:

trans-4-isopropylpyrrolidine-3-carboxylic acid;

trans-4-propyl-pyrrolidine-3-carboxylic acid; and trans-4-butyl-pyrrolidine-3-carboxylic acid.

8. A pharmaceutical composition comprising a therapeutically effective amount of a compound according to claim 1 and a pharmaceutically acceptable carrier.

9. A method for treating epilepsy comprising administering a therapeutically effective amount of a compound according to claim 1 to a mammal in need of said treatment.

10. A method for treating faintness attacks, hypokinesia, and cranial disorders comprising administering a therapeutically effective amount of a compound according to claim 1 to a mammal in need of said treatment.

11. A method for treating neurodegenerative disorders comprising administering a therapeutically effective amount of a compound according to claim 1 to a mammal in need of said treatment.

12. A method for treating depression comprising administering a therapeutically effective amount of a compound according to claim 1 to a mammal in need of said treatment.

13. A method for treating anxiety comprising administering a therapeutically effective amount of a compound according to claim 1 to a mammal in need of said treatment.

14. A method for treating panic comprising administering a therapeutically effective amount of a compound according to claim 1 to a mammal in need of said treatment.

15. A method for treating pain comprising administering a therapeutically effective amount of a compound according to claim 1 to a mammal in need of said treatment.

16. A method for treating neuropathological disorders comprising administering a therapeutically effective amount of a compound according to claim 1 to a mammal in need of said treatment.

* * * * *